United States Patent
Scott et al.

(10) Patent No.: US 7,292,885 B2
(45) Date of Patent: Nov. 6, 2007

(54) MECHANICAL APPARATUS AND METHOD FOR DILATING AND DELIVERING A THERAPEUTIC AGENT TO A SITE OF TREATMENT

(75) Inventors: Neal Scott, Houston, TX (US); Jerome Segal, Chevy Chase, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 580 days.

(21) Appl. No.: 10/135,709

(22) Filed: Apr. 30, 2002

(65) Prior Publication Data

US 2003/0100887 A1    May 29, 2003

Related U.S. Application Data

(63) Continuation-in-part of application No. 09/997,855, filed on Nov. 29, 2001, now abandoned.

(51) Int. Cl.
*A61N 1/30* (2006.01)
*A61M 29/00* (2006.01)

(52) U.S. Cl. ......................... 604/21; 604/104
(58) Field of Classification Search ............. 604/93.01, 604/20, 21, 104–109, 501
See application file for complete search history.

(56) References Cited

U.S. PATENT DOCUMENTS

| | | |
|---|---|---|
| 3,993,754 A | 11/1976 | Rahman |
| 4,749,585 A | 6/1988 | Greco et al. |
| 5,034,001 A | 7/1991 | Garrison et al. |
| 5,264,618 A | 11/1993 | Felgner et al. |
| 5,282,785 A | 2/1994 | Shapland |
| 5,286,254 A | 2/1994 | Shapland |
| 5,304,120 A | 4/1994 | Hofman |
| 5,423,744 A | 6/1995 | Gencheff et al. |
| 5,443,495 A * | 8/1995 | Buscemi et al. ........... 623/1.21 |
| 5,498,238 A | 3/1996 | Shapland |
| 5,499,971 A | 3/1996 | Shapland et al. |
| 5,507,724 A | 4/1996 | Hofman |
| 5,527,282 A | 6/1996 | Segal |
| 5,607,691 A * | 3/1997 | Hale et al. .................. 424/449 |
| 5,628,730 A | 5/1997 | Shapland |
| 5,634,899 A | 6/1997 | Shapland |
| 5,704,908 A | 1/1998 | Hofman |
| 5,807,306 A * | 9/1998 | Shapland et al. ............. 604/21 |
| 5,865,787 A | 2/1999 | Shapland |
| 5,866,561 A | 2/1999 | Ungs |

(Continued)

FOREIGN PATENT DOCUMENTS

WO    WO 94/05361 A    3/1994

(Continued)

*Primary Examiner*—Catherine S. Williams
(74) *Attorney, Agent, or Firm*—Kenyon & Kenyon LLP

(57) ABSTRACT

A mechanical dilatation and medicament delivery device for enlarging a flow passage of a vessel by dilating and delivering a liposome or micelle-encapsulated therapeutic agent or medicament to an obstruction in the vessel. The present invention comprises a substantially cylindrically shaped expansion member and includes a means engaged to the expansion member for altering the distance between the proximal end and the distal end of the expansion member thereby transforming the expansion member between a diametrically contracted configuration to diametrically expanded configuration. A liposome or micelle-encapsulated therapeutic agent or medicament is coated on either the expansion member, or incorporated into a substrate coated on the expansion member.

19 Claims, 5 Drawing Sheets

U.S. PATENT DOCUMENTS

| | | |
|---|---|---|
| 5,935,598 A | 8/1999 | Sage et al. |
| 5,972,600 A | 10/1999 | Szoka |
| 5,985,307 A | 11/1999 | Hanson et al. |
| 6,048,545 A | 4/2000 | Keller et al. |
| 6,120,799 A | 9/2000 | McDonald et al. |
| 6,136,846 A * | 10/2000 | Rubinfeld et al. .......... 514/449 |
| 6,142,987 A | 11/2000 | Tsugita |
| 6,219,577 B1 | 4/2001 | Brown, III et al. |
| 6,228,393 B1 | 5/2001 | DiCosmo et al. |
| 6,280,411 B1 | 8/2001 | Lennox |
| 6,369,039 B1 | 4/2002 | Palasis et al. |
| 6,450,984 B1 | 9/2002 | Lynch et al. |
| 2003/0100887 A1 | 5/2003 | Scott et al. |

FOREIGN PATENT DOCUMENTS

| | | |
|---|---|---|
| WO | WO 01/54748 A | 8/2001 |

* cited by examiner

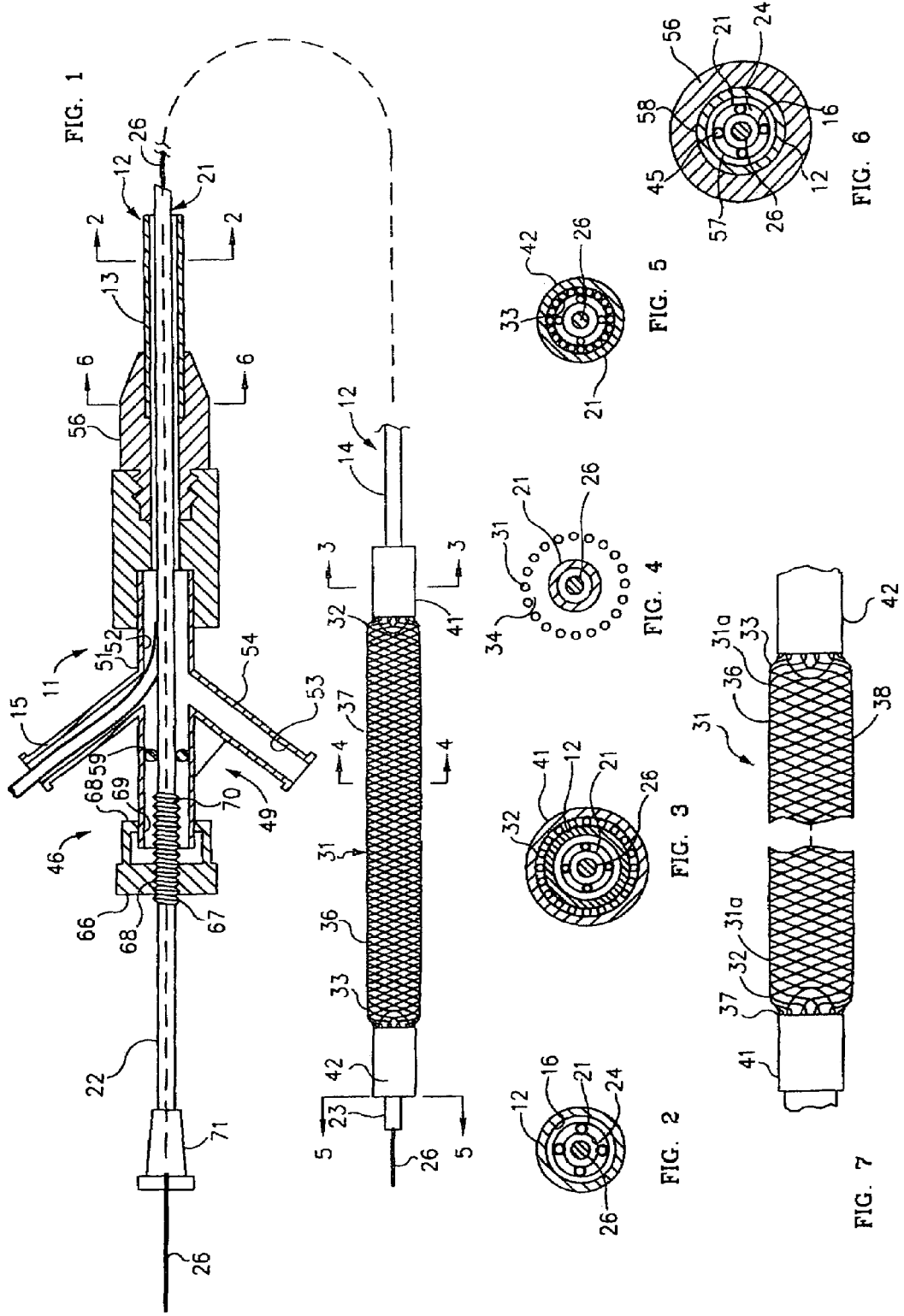

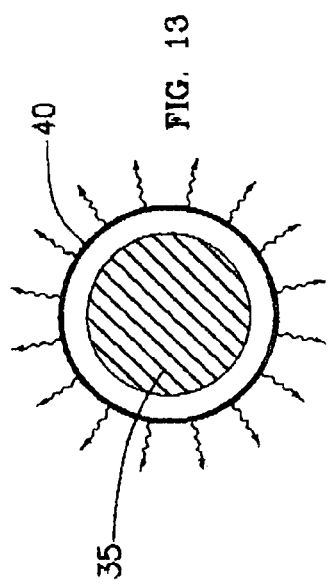
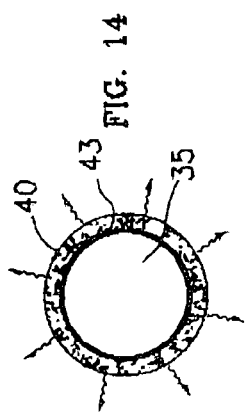
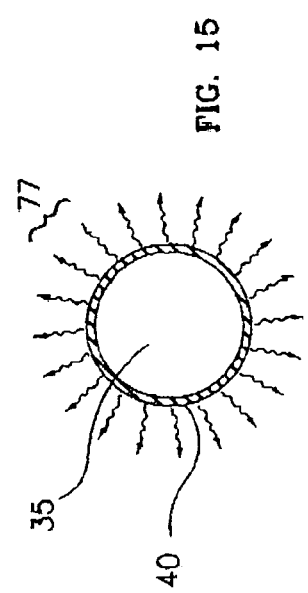
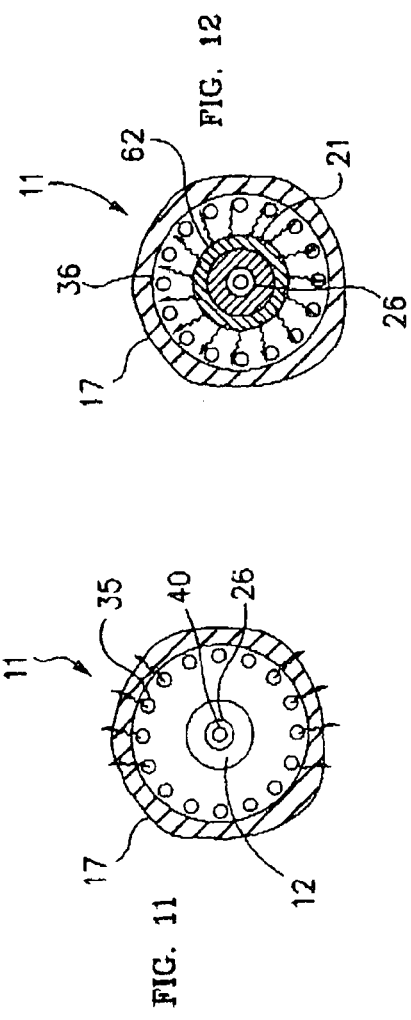

Figure 17
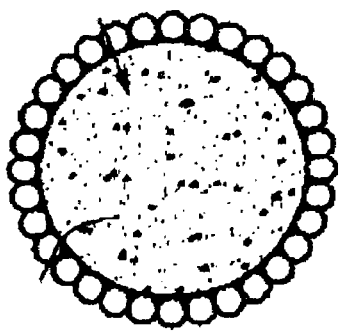
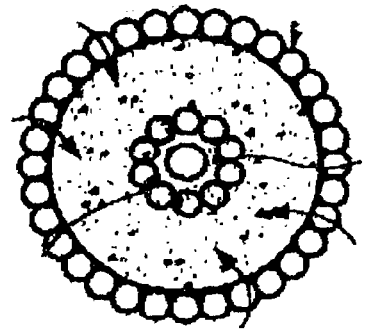

MECHANICAL APPARATUS AND METHOD FOR DILATING AND DELIVERING A THERAPEUTIC AGENT TO A SITE OF TREATMENT

PRIOR APPLICATIONS

This application is a continuation-in-part of application Ser. No. 09/997,855 filed on Nov. 29, 2001 now abandoned.

BACKGROUND OF THE INVENTION

Cardiovascular disease is commonly accepted as being one of the most serious health risks facing our society today. Diseased and obstructed coronary arteries can restrict the flow of blood and cause tissue ischemia and necrosis. While the exact etiology of sclerotic cardiovascular disease is still in question, the treatment of narrowed coronary arteries is more defined. Surgical construction of coronary artery bypass grafts (CABG) is often the method of choice when there are several diseased segments in one or multiple arteries. Open heart surgery is, of course, very traumatic for patients. In many cases, less traumatic, alternative methods are available for treating cardiovascular disease percutaneously. These alternate treatment methods generally employ various types of percutaneous transluminal angioplasty (PTCA) balloons or excising devices (atherectomy) to remodel or debulk diseased vessel segments. A further alternative treatment method involves percutaneous, intraluminal installation of expandable, tubular stents or prostheses in sclerotic lesions.

A recurrent problem with the previous devices and PTCA procedures is their failure to maintain patency due to the growth of injured vascular tissue. This is known as "restenosis" and may be a result of the original injury to the vessel wall occurring during the angioplasty procedure. Pathologically restenosis represents a neointimal proliferative response characterized by smooth muscle cell hyperplasia that results in reblockage of the vessel lumen necessitating repeat PTCA procedures up to 35-50% of all cases. It has been generally accepted that a certain therapeutic agents or medicaments may be capable of selectively inhibiting the growth of these hyperproliferating smooth muscle cells and thereby reduce the rate of restenosis after the primary interventional procedure.

Heretofore, various devices have been disclosed which may be used to deliver a therapeutic agent or medicament to a blood vessel while undergoing angioplasty. Balloon angioplasty catheters have been used to place and deliver a various therapeutic agents or medicaments within human vessels. For example, in U.S. Pat. Nos. 5,112,305, 5,746,716, 5,681,281, 5,873,852, 5,713,863 and 6,102,904 disclose and claim a balloon catheter system with various injector plates mounted on the balloon for delivering a drug into an arterial segment.

Alternatively a standard angioplasty balloon may be coated with a polymeric material which is then used to bond certain medicaments or theraputic agents. These agents are then delivered to the desired therapeutic site by inflation of the balloon and diffusion of the medicatment or therapeutic agent into the vessel wall. Only limited quantities of therapeutic agents can be delivered because of "wash-out" of the drug into the circulation during balloon placement and due to the limited time the inflated balloon can be left in place due to ischemia caused by the balloon.

In addition, previously disclosed methods of delivering drug to a site of treatment are described which utilize iontophoretic or electrophoretic means as disclosed in U.S. Pat. No. 5,499,971. Using these iontophoretic or electroporetic means passive diffusion of the drug or medicament is enhanced by placing the medicament or theraputic agent in close proximity to the site of treatment and then using electrically to augment delivery of the drug into the tissues or cells. These methods generally place the drug inside a balloon mounted distally on a catheter whereby the balloon is composed of a semi-porous material through which the drug can diffuse.

Alternatively the electrodes themselves may be used as a method for iontophoretic or electroporetic drug delivery. One such method is disclosed in U.S. Pat. No. 6,219,577 which describes coating the surface of band-like electrodes with a polymer which bonds the drug and delivers it to the site of treatment. This method has the disadvantage of not have the capability to dilate the obstruction prior or concurrent to the delivery of a drug. Additionally the surface area of contact of the electrode bands with the vessel wall are limited to only the central portion of the arc shaped bands. This limits the contact surface area of the drug coated electrodes. This method also has the inherent disadvantage that since the site of therapy is intravascular, most of the drug will be washed off or dissolved off the electrodes into the circulating blood stream before it is advanced through the vascular system from its percutaneous entry and to the distal site of treatment. This again limits the amount of the drug delivered to the site and also potentially subjects the patient to harmful or toxic systemic exposure.

Additional devices have been disclosed which attempt to improve the depth of penetration into tissue by pressure driving a solution of the drug into the vessel wall through small orifices in the balloon material. There is, however, some evidence that high pressure "jetting" of a drug solution out of small pores close to the vessel lumen can in fact cause vessel wall injury. The development of double skinned, microporous (or weeping) balloons obviated this "jetting" effect to some extent, but diffusion of the drug into the vessel wall is still slow, and much of the drug can be lost through subsequent "washout effects". This method leads to limited amounts of drugs or therapeutics agents delivered to the tissues or cells. Furthermore, in all of these methods the balloon must be expanded and thereby restricts blood flow to the distal arterial segments while the balloon is in the expanded configuration thus limiting the time the drug delivering balloon can be clinically utilized.

There are also several disadvantages using either a stent or balloon catheter to delivery a therapeutic agent or medicament to a vascular segment. Regarding the therapeutic agent eluting stents, once the stent is deployed, there is no means outside of invasive surgical excision, to remove the eluting stent from the vascular segment. Therefore, stents or implanted prostheses with therapeutic agent eluting properties must be precisely calibrated to deliver an exact quantity of the therapeutic agent or medicament to the vascular segment upon stent deployment. Balloon catheters employed to delivery a therapeutic agent or medicament to a vascular segment have limitations including potential balloon rupture and ischemia due to balloon inflation limiting distal blood flow to the artery. This leads to tissue ischemia and potential necrosis. Even "perfusion" type angioplasty balloons used to delivery a therapeutic agent or medicament to the affected artery provide far less than physiological blood flow during balloon inflation and dwell times are limited by ischemia and tissue necrosis.

Recent studies have demonstrated the effectiveness of a number of agents (e.g., paclitaxel, rapamycin, Actinomycin D) on the prevention of unwanted cellular proliferation. These agents have proven efficacy in the treatment of cancer and transplant rejection. A major advantage of these agents is the high lipid solubility that causes tissue levels to be high for an extended period of time since they cannot be rapidly cleared. However, this advantage is also a disadvantage because the delivery of these medicaments must generally pass hydrophilic boundaries.

Thus, it can be seen that there is a need for a new and improved device to selectively delivery a therapeutic agent or medicament to an arterial segment and which overcomes these disadvantages.

In general, it is an object of this present invention to provide a mechanical dilatation device and method which is capable of dilating an obstruction within a vascular segment while delivering, either passively or by an electrically active means, a therapeutic agent or medicament to the vessel segment.

Another object of the invention is to provide a method to deliver high concentrations of agents that are poorly soluble or insoluble in aqueous media to selected sites in the body including arteries, veins or other tubular structures, prosthetic devices such as grafts, and tissues such as, but not limited to, brain, myocardium, colon, liver, breast and lung.

Another object of the invention is to provide a percutaneous device and method of the above character which can be used for prolonged periods in exposing or delivering a therapeutic agent or medicament to a vascular segment while allowing continuous perfusion of blood into the vessel distal to the treatment area.

Another object of the invention is to provide a device that can control the release or diffusion of a medicament or therapeutic agent to minimize potential systemic affects and maximize the diffusion or delivery of the medicament or therapeutic agent to the site of treatment.

Another object of the invention is to provide a device that is not susceptible to structural damage (balloon rupture) and subsequent release of therapeutic agents or drug materials into the vasculature.

SUMMARY OF THE INVENTION

It is known that therapeutic agent therapy can reduce the proliferation of rapidly growing cells. The present invention employs various means of delivery with a mechanical dilatation device for enlarging a flow passage of a vessel by dilating and delivering a liposome or micelle or micelle-encapsulated therapeutic agent or medicament to an obstruction in a vessel. Since the therapeutic agent or medicament is capable of selectively inhibiting the growth of proliferating cells, the present invention not only achieves acute patency of a vessel but employs medical therapy to maintain chronic patency through the prevention of restenosis.

The present invention comprises a substantially cylindrically shaped expansion member and includes a means engaged to the expansion member for altering the distance between the proximal end and the distal end of the expansion member thereby transforming the expansion member between a diametrically contracted configuration and a diametrically expanded configuration. A liposome or micelle-encapsulated therapeutic agent or medicament can be coated directly on the expansion member or alternatively, the therapeutic agent or medicament can be incorporated into a polymer or other substrate coated on the expansion mesh. If desired, the same or another therapeutic agent or medicament can be coated on the marker bands mounted on the catheter located within the expansion mesh or injected through a delivery lumen which has a distal port located inside the expansion member. Due to its unique design, the present invention has significant perfusion capability which allows the catheter and its distal expansion member or mesh to be in a expanded configuration and engaged to the vessel wall for prolonged periods. This allows sufficient time for passive or electrically active migration of the therapeutic agent or medicament to the vessel or organ without causing ischemic related events. The catheter also comprises either an over-the-wire or rapid exchange designs.

The present invention also can include a conduction means that provides electrical communication from a connector on the proximal end of the catheter to the distal conductive flexible elongate elements thereby providing the distal expandable mesh with a means to control or facilitate the release or delivery of a medicament or therapeutic agent to a treatment site. In this embodiment, the invention relates to catheter-based devices which provide an electrical driving force that can increase the rate of migration of liposome or micelle-encapsulated medicaments and other therapeutic agents from the expansion member and into body tissues and cells using iontophoresis only, electroporation only, or combined iontophoresis and electroporation. In addition, a charge can be applied to the expansion member that is opposite the liposome or micelle-encapsulated therapeutic agent or medicament, or to the substrate that incorporates the therapeutic agent or medicament in order to create a significant bond between the therapeutic agent and the expandable mesh.

The invention also takes advantage of the prior body of knowledge that has demonstrated the enhanced solubility and delivery of agents after they have been incorporated into liposome or micelles or micelles. Since liposome or micelles and micelles possess both lipophilic and hydrophilic regions, they can be used to solubilize compounds that are insoluble in water. If charged liposome or micelles are used, these charged molecules can move in an electrical field.

This disclosure demonstrates the delivery of uncharged, lipophilic medicaments or agents by incorporating them into charged liposome or micelles and then delivering them to the target site by electrophoresis.

The present method also comprises the steps of advancing the catheter and expansion member to the obstruction in a vessel and applying opposed forces on said expansion member in an axial direction to move the expansion member to an expanded configuration wherein the expansion member dilates the obstruction and the catheter/expansion member assembly actively (or passively) delivers the liposome or micelle-encapsulated therapeutic agent or medicament to the obstruction.

One preferable approach may be to 1) energize the catheter to create a bond between the therapeutic agent and expansion mesh and then advance the system to the treatment segment, 2) expand the expansion member to dilate the segment, 3) allow perfusion to passively transfer the therapeutic agent into the tissues.

Another preferable approach may be to 1) energize the catheter to create a bond between the liposome or micelle enclosed therapeutic agent and expansion mesh and then advance the system to the treatment segment, 2) expand the expansion member to dilate the segment while allowing perfusion, 3) apply electrical energy to cause iontophoresis of the therapeutic agent into the tissues and/or 4) apply electrical energy for electroporation to be applied to permeabilize the cells. Preferably, the catheter is able to perform steps 2, 3 and 4 sequentially without repositioning of the catheter. Even more preferably, the catheter is designed to maintain a high concentration of drug in the tissue extracellular spaces (e.g. by iontophoresis) such that the subsequent creation of transient pores in cell surface membranes by electroporation pulses results in greatly improved intracellular delivery of the medicament or therapeutic agent.

BRIEF DESCRIPTION OF THE DRAWINGS

FIG. 1 is a side-elevational view partially in section of a mechanical dilatation and medicament delivery device incorporating the present invention.

FIG. 2 is a cross-sectional view taken along the line 2-2 of FIG. 1 demonstrating the electrical connection means.

FIG. 3 is a cross-sectional view taken along the line 3-3 of FIG. 1 demonstrating the electrical connection means.

FIG. 4 is a cross-sectional view taken along the line 4-4 of FIG. 1.

FIG. 5 is a cross-sectional view taken along the line 5-5 of FIG. 1 demonstrating the electrical connection means.

FIG. 6 is a cross-sectional view taken along the line 6-6 of FIG. 1 demonstrating the electrical connection means.

FIG. 7 is a greatly enlarged view of a portion of the dilatation and medicament delivery device in a partially expanded state.

FIG. 11 is a cross sectional view of the flexible elongated elements demonstrating the passive or electrically active dispensing of the liposome or micelle-encapsulated therapeutic agent or medicament into the vessel wall.

FIG. 12 is a cross sectional view demonstrating the dispensing of a liposome or micelle-encapsulated therapeutic agent or medicament from bands affixed to the inner tubular member located within the expandable mesh.

FIG. 13 is a cross sectional view of the one flexible elongate elements of the expandable mesh demonstrating the passive or electrically active dispensing of a liposome or micelle-encapsulated therapeutic agent or medicament from the elongate element.

FIG. 14 is a cross sectional view of one of the flexible elongate elements of the expandable mesh demonstrating the dispensing of the liposome or micelle-encapsulated therapeutic agent or medicament incorporated within a substrate coating over the elongate element.

FIG. 15 is a cross sectional view of one of the flexible elongate elements of the expandable mesh demonstrating the dispensing of a liposome or micelle-encapsulated therapeutic agent or medicament with the aid of electrical current.

FIG. 16 is a cross sectional side view of the flexible elongated elements demonstrating the passive or electrically active dispensing of the liposome or micelle-encapsulated therapeutic agent or medicament into the vessel wall.

FIG. 17 is a cross section side view of a typical liposome or micelle encapsulating a generic medicament.

DETAILED DESCRIPTION OF THE DRAWINGS

Figure 8A:
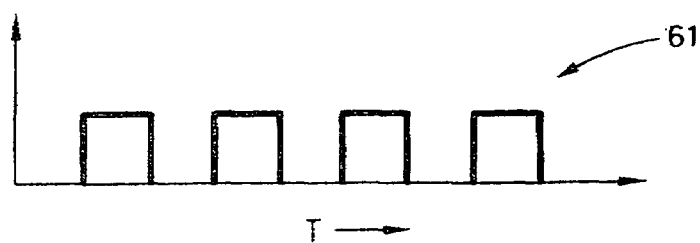
FIGS. 8a-8f depict a variety of electric waveforms for use in iontophoresis and electrophoresis with the catheter and distal mesh of the present invention.
Figure 8B:
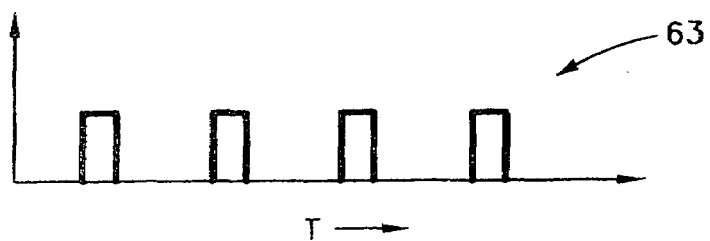
Figure 8C:
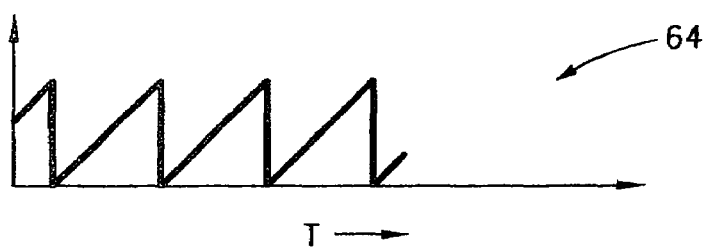
Figure 8D:
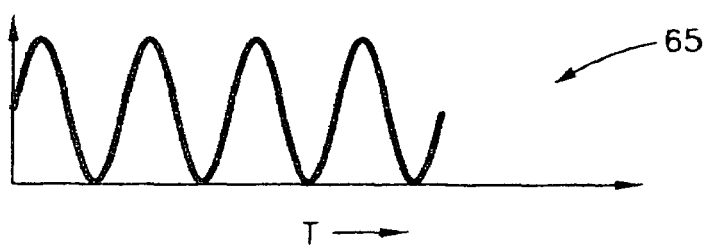
Figure 8E:
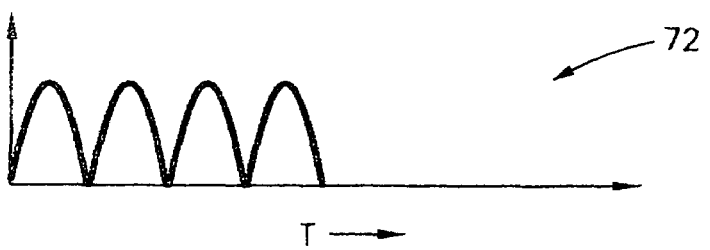
Figure 8F:
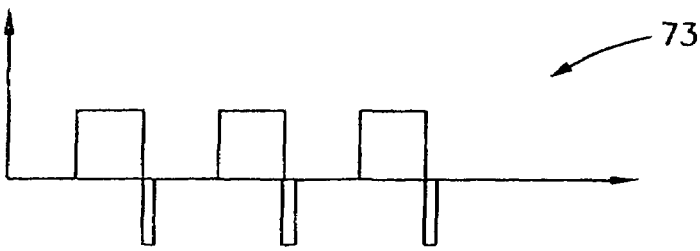

In general, the present invention relates generally to devices that are used to dilate and dispense a medicament or therapeutic agent to an obstruction within a stenotic segment of a vessel. The device is comprised of an cylindrical expansion member to be disposed in an obstruction in a vessel carrying flowing blood. The cylindrical expansion member has first and second ends and an intermediate portion between the first and second ends. The cylindrical expansion member also has a flow passage extending therethrough with a diameter and a longitudinal central axis. The diameter of the flow passage is a variable with movement of the first and second ends relative to each other along the longitudinal central axis from a diametrically contracted position to a diametrically expanded condition. The cylindrical expansion member is comprised of a plurality of flexible elongate elements each of which extends helically about the longitudinal extending central axis. The flexible elongate elements are coated with one or more liposome or micelle-encapsulated medicaments, therapeutic agents, drugs, pharmaceuticals, plasmids, genes or other agents. For the purposes of this application, the terms used, liposome or micelle-encapsulated medicaments and therapeutic agents, will be used to encompass all the particular agents described herein. It is also contemplated that the liposome or micelle-encapsulated medicament or therapeutic agent may be incorporated with a non-medicament substrate that has been previously or simultaneously coated on the flexible elongate elements. Furthermore, an electrical means can be incorporated into the catheter system to cause 1) electrical bonding of the therapeutic agent to the mesh and/or 2) active migration/dispersion of the agent into the vessel/tissues. In addition, the present invention can include coating one or more of the bands secured to the central catheter element within the expansion mesh with one or more therapeutic agents.

The plurality of the flexible elongate elements of the expansion mesh have a first common direction of rotation are axially displaced relative to each other and cross a further plurality of the flexible elongate elements also axially displaced relative to each other but having a second common direction opposite to that of the first direction of rotation to form a braided cylindrical expansion member. The crossing of the flexible elongate elements occurs in an area of contact between the flexible elongate elements.

First and second altering means are provided respectively for engaging the first and second ends of said cylindrical expansion member for retaining said first and second ends in contracted positions. Altering means are provided for causing relative axial movement of the first and second ends towards each other to cause the intermediate cylindrical portion of the expansion member to contract longitudinally and to expand diametrically by causing the flexible elongate elements in the intermediate portion of the cylindrical member to move closer to each other expanding the diametric dimensions of the cylindrical expansion member thereby allowing it to contact the vessel wall and enable it to dilate an obstruction within the vessel. Flexible elongate elements at the first and second ends of the cylindrical expansion member remain contracted around and within first and second means and are thereby prevented from moving closer which maintains spacing between the flexible elongate members so that blood in the vessel can continue to flow through the first and second ends and through the flow passage in the cylindrical expansion member while the cylindrical expansion member is in engagement with vessel wall and dilating an obstruction within the vessel.

More in particular as shown in FIGS. 1-7 of the drawings, the mechanical dilatation and medicament delivery device 11 shown therein consists of a first or outer flexible elongate tubular member 12 having proximal and distal extremities 13 and 14 with the flow passage 16 extending from the proximal extremity 13 to the distal extremity 14. FIGS. 2a, 3a, 5a, and 6a are provided to represent the embodiment that includes an electrical conduction means extending from the proximal connector and engaged to the distal expansion member 31. A second or inner flexible tubular member 21 is coaxially and slidably disposed within the flow passage 16 of the first or outer flexible elongate tubular member 12 and is provided with proximal and distal extremities 22 and 23 with a flow passage 24 extending from the proximal extremity 22 to the distal extremity 23. If the flexible elongate elements of the dilating member are made of a metallic material such as stainless steel, elgiloy or other conductive material, an electrical lead can be connected to the mesh to make it part of the circuit. The electrical lead can either run along or within one of the lumens of the catheter or can be in the form of a braid that is made of a conductive material and have generally functions to provide reinforcement to the catheter shaft. A second electrode could be placed on the distal tip of the catheter via a small band with its electrical lead running down one of the lumens to the proximal end of the catheter. Alternatively, the electircal lead could be engaged to the patient's skin or could be the guidewire over which the catheter is routinely advanced.

The flexible elongate elements of the catheter could be coated with a polymeric material or similar substrate onto which the liposome or micelle-encapsulated medicament or theraputic agent could adsorb. Synthetic polymers or natural polymers can be used, such as amino acid polymers or polysaccharides. The polymer is selected depending on the therapeutic agent required, the polymer's compatibility with a patient and the ultimate pharmacologic effect desired. These polymers could include hydrophilic polymers used for their absorptive properties of aqueous solutions. The flexible elongate elements, either coated or uncoated, could then be submerged in a solution of a liposome or micelle-encapsulated therapeutic agents or medicaments with a specific charge and an electrical charge could be applied to render the flexible elongate members opposite in charge to that of the liposome or micelle-encapsulated therapeutic agent or medicament. This would create a significant bonding of the liposome or micelle-encapsulated agent or medicament to the flexible elongate elements. Typically, the flexible elongate elements of the mesh will be charged with the attached liposome or micelle-encapsulated therapeutic agent or medicament just prior to advancing the catheter through the patient's vasculature to the site of dilatation and therapy without significant loss of the drug in the bloodstream. Once the site of obstruction or treatment is reached, the charge on the mesh could be reversed using the same electrodes thus driving the liposome or micelle-encapsulated therapeutic agent or medicament into the target tissue. In this case, the electrode placed on the skin of the patient would be used to cause active diffusion or iontophoresis of the therapeutic agent or medicament into the target tissues. As shown in FIGS. 8a-8f, the present invention can employ flow of electrical current in the from of various waveforms to perform the iontophoresis and/or electroporation procedures. Possible waveforms contemplated for the present invention include square waves, rectangular waves, saw-toothed waves, sinusoidal waves that do not reverse polarity, rectified sinusoidal waves, and other waveform shapes which may reverse polarity but provide a net flow of current in the desired direction.

Electrical current could also be coordinated with the patient's elctrocardiogram such that electrical current is provided to the mesh only during certain phases of cardiac depolarization. This "gating" of the electrical current would avoid the potential danger of discharging electrical current to the heart during vunerable phases of depolarization which may lead to cardiac arrhythmias.

Iontophoretically enhanced delivery requires that the therapeutic agent carry a net charge under physiological conditions whereas electroporation alone would be used for delivering treatment agents that are not sufficiently ionized to iontophorese well into tissues. Electroporation may also be the preferred strategy for enhancing localized cellular targeting of a systemically administered therapeutic agent.

As used herein, the term "iontophoresis" means the migration of ionizable molecules through a medium driven by an applied low-level electrical potential. This electrically mediated movement of molecules into tissues is superimposed upon concentration gradient dependent diffusion processes. If the medium or tissue through which the molecules travel also carries a charge, some electro-osmotic flow occurs. However, generally, the rate of migration of molecules with a net negative charge towards the positive electrode and vice versa is determined by the net charge on the moving molecules and the applied electrical potential. The driving force may also be considered as electrostatic repulsion. Iontophoresis usually requires relatively low constant DC current in the range of from about 2-10 mA. In a well established application of iontophoresis, that of enhancing drug delivery through the skin (transdermal iontophoresis), one electrode is positioned over the treatment area and the second electrode is located at a remote site, usually somewhere else on the skin. With the present invention the return electrode may be similarly positioned on the skin. Alternatively the tip of the guide wire emerging from the distal end of the support catheter may serve as the return electrode.

As used herein, the term "electroporation" means the temporary creation of holes or aqueous pores in the surface of a cell membrane by an applied electrical potential and through which therapeutic agents may pass into the cell. Electroporation is now widely used in biology, particularly for transfection studies, where plasmids, DNA fragments and other genetic material are introduced into living cells. During electroporation pulsing, molecules that are not normally membrane permeant are able to pass from the extracellular environment into the cells during the period of induced reversible membrane permeabilization. The permeabilized state is caused by the generation of an electrical field in the cell suspension or tissue of sufficient field strength to perturb the cell surface membrane's proteolipid structure. This perturbation (sometimes referred to as dielectric breakdown) is believed to be due to both a constituent charge separation and the effect of viscoelastic compression forces within the membrane and it's sub-adjacent cytoskeletal structures. The result is a localized membrane thinning. At a critical external field strength, pores or small domains of increased permeability are formed in the membrane proteolipid bi-layer.

A guide wire 26 of a conventional type is adapted to be introduced through the flow passage 24 in the inner flexible elongate tubular member for use in guiding the mechanical dilatation and medicament delivery device 11 as a over-the-wire design as hereinafter described. The guide wire 26 can be of a suitable size as for example 0.010"-0.035" and can have a suitable length ranging from 150 to 300 centimeters. For example, the first or outer flexible elongate tubular member 12 can have an outside diameter of 0.6-3 millimeters with a wall thickness of 0.12 millimeters to provide a flow passage of 0.75 millimeters in diameter. Similarly, the second or inner flexible elongate tubular member 21 can have a suitable outside diameter as for example 0.6 millimeters with a wall thickness of 0.12 millimeters and a flow passage 24 of 0.45 millimeters in diameter. The flexible elongate tubular members 12 and 21 can be formed of a suitable plastic as for example a polyimide, polyethylene, Nylon or polybutylterphalate (PBT).

In accordance with the present invention an essentially cylindrically shaped expansion member 31 is provided which has a first or proximal end 32 and a second or distal end 33 with a central or inner flow passage 34 extending from the proximal end 32 to the distal end 33 along a longitudinally extending central axis and has a diameter which is a variable as hereinafter described. The cylindrically shaped expansion member 31 is comprised of a plurality of flexible elongate elements or filaments 36 each of which extends helically about the longitudinally extending central axis. The flexible elongate elements 36 are formed of suitable materials which can be utilized in the human blood as for example stainless steel, Nitinol, Aermet™, Elgiloy™ or certain other plastic fibers. The flexible elongate elements 36 can have a suitable diameter as for example 0.001 to 0.010 inches or can be configured as a round, elliptical, flat or triangular wire ribbon. A plurality of the flexible elongate elements 36 have a first common direction of rotation about the central axis as shown in FIGS. 1 and 7 are axially displaced relative to each other and cross a further plurality of the flexible elongate elements 36 also axially displaced relative to each other but having a second common direction of rotation opposite to that of the first direction of rotation to form a double helix or braided or mesh-like cylindrical expansion member with the crossing of flexible elongate elements 36 occurring in the area of contact between the flexible elongate elements to form openings or interstices 37 therebetween. Thus the flexible elongate elements 36 form an expansion member 31 which provides a central or inner flow passage 34 which is variable in diameter upon movement of the first and second ends of the expansion member 31 relative to each other along the longitudinally extending central axis.

Means is provided for constraining the first and second or proximal and distal ends 32 and 33 of the expansion member 31 and consists of a first or proximal collar 41 and a second or distal collar 42. The first and second collars 41 and 42 are formed of a suitable material such as a polyimide. The first or proximal collar 41 has a suitable length as for example 1.0 to 5.0 millimeters and is sized so that it can fit over the first or proximal end 32 of the expansion member 31 when it is in a contracted position and over the distal extremity 14 of the first or outer flexible elongate member 12. In order to ensure that elongate elements or filaments 36 of the first or proximal extremity 32 are firmly secured to the distal extremity 14 of the first or outer flexible elongate member 12, an adhesive can be provided bonding the first or proximal end 32 to the collar 41 and to the distal extremity 14 of the first or outer flexible elongate tubular member 12. The second or distal collar 42 can be of a suitable size and typically may be slightly smaller in diameter because it need merely secure the elongate element or filaments 36 of the distal end 33 of the expansion member 31 to the distal extremity 23 of the second or inner flexible elongate tubular member 21. An adhesive (not shown) is provided to firmly secure the second or distal end 33 of the expansion member 31 between the second or distal collar 42 and the distal extremity of the inner flexible elongate tubular member 21. In this manner it can be seen that the cylindrical expansion member 31 has its proximal end curved conically inward toward and secured to the distal extremity of the outer flexible elongate tubular member 12 and the second or distal end 33 of the expansion member 31 also curves conically inward toward and is secured to the distal extremity of the second or inner flexible elongate tubular member 21.

Typically the distance between the first and second collars 41 and 42 can range from between 5 to 150 millimeters. Typically the distal end 23 of the second or inner flexible elongate tubular member 21 extends approximately 5-170 millimeters beyond the distal extremity 14 of the first or outer flexible elongate tubular member 12.

It can be seen that by moving the first or outer flexible elongate tubular member 12 and the second inner flexible elongate tubular member 21 axially with respect to each other, the first and second ends of the expansion member 31 are moved towards each other causing the elongate elements or filaments 36 of an intermediate portion of the cylindrical expansion member between the first and second ends to move closer to each other to cause these flexible elongate elements to move into apposition with each other and to expand in a first radial direction the intermediate portion of the cylindrical expansion member 31 (FIG. 7) and to cause the diameter of the central flow passage 34 to increase. The portions of the expansion member 31 immediately adjacent the first and second collars 41 and 42 remain restrained by the collars 41 and 42 causing the flexible elongate elements 36 immediately adjacent to the collars 41 and 42 to curve conically toward and remain crossed and unable to come into close apposition and thereby provide openings or interstices 37 therebetween, which remain relatively constant in shape and size so that blood can flow from the first and second ends 32 and 33 through the central or inner flow passage 34 as hereinafter described.

The essentially cylindrical shape of the expansion member when expanded in a radial directon provides an enlarged surface of contact between the expansion member and the vessel wall or obstruction. This enlarged surface of contact enables the cylindrical expansion member to deliver an amount of medicament or therapeutic agent which is present on the surface of the flexible elongate elements that comprise the expansion member. This delivery of medicament or therapeutic agent may be by the various well known means previously described such as passive or electrically active diffusion, pressure, iontophoresis or electroporesis.

One example of the means provided in the mechanical dilatation and medicament delivery device 11 for causing relative movement between the first or outer flexible elongate tubular member 12 and the second or inner flexible elongate tubular member 21 and consists of a linear movement mechanism 46. The linear movement mechanism 46 includes a Y-adapter 49 that is provided with a central arm 51 having a lumen 52 through which the second or inner flexible elongate tubular member 21 extends. The lumen or flow passage 52 is in communication with the lumen 16 of outer flexible elongate tubular member 12 and with a flow passage 53 in a side arm 54 which is adapted to receive a syringe (not shown) so that saline, radiocontrast liquid or a medicament/therapeutic agent can be introduced through the side arm 54 and into the flow passage 52 in the Y-adapter 49 and thence into lumen 16 of outer member 12. The distal end of screw mechanism 46 is provided with a fitting 56 with inner lumen 57 into which the proximal end 13 of flexible elongate tubular member 12 is seated and held in place by an adhesive 58 at the distal end of fitting 56. Lumen 57 is thereby in communication with flow passage 52 of central arm 51 and with flow passage 53 of side arm 54. An O-ring 59 that is adapted to form a fluid-tight seal with respect to the second or inner flexible tubular member 21 is disposed in the lumen 52 of the central arm 51. An interiorly threaded knurled knob 66 is threaded onto an exteriorly threaded member 67 which is secured to and surrounds the proximal extremity 22 of inner flexible elongate tubular member 21. The knob 66 is provided with an inwardly extending flange 68 which seats in an annular recess 69 in the central arm 51. Thus, rotation of the knob 66 causes advancement or retraction of threaded member 67 and the second or inner flexible elongate tubular member 21 with respect to the fitting 56. Indicia 68 in the form of longitudinally spaced-apart rings 70 are provided on the member 67 and serve to indicate the distance that the second or inner flexible elongate tubular member 21 has been advanced and retracted with respect to the first or outer flexible elongate member 12.

A Luer-type fitting 71 is mounted on the proximal extremity 22 of the inner elongate flexible tubular member 21 and is adapted to be engaged by a finger of the hand. The guide wire 26 extends through the fitting 71 and into the lumen 24 of inner elongate flexible tubular member 21.

It should be appreciated that even though one particular linear movement mechanism 46 has been provided for advancing and retracting the flexible elongate members 12 and 21 with respect to each other, other mechanisms also can be utilized if desired to provide such relative movement. Other possible designs that could be employed are scissors-jack, rachet-type or straight slide mechanisms.

Figure 9:
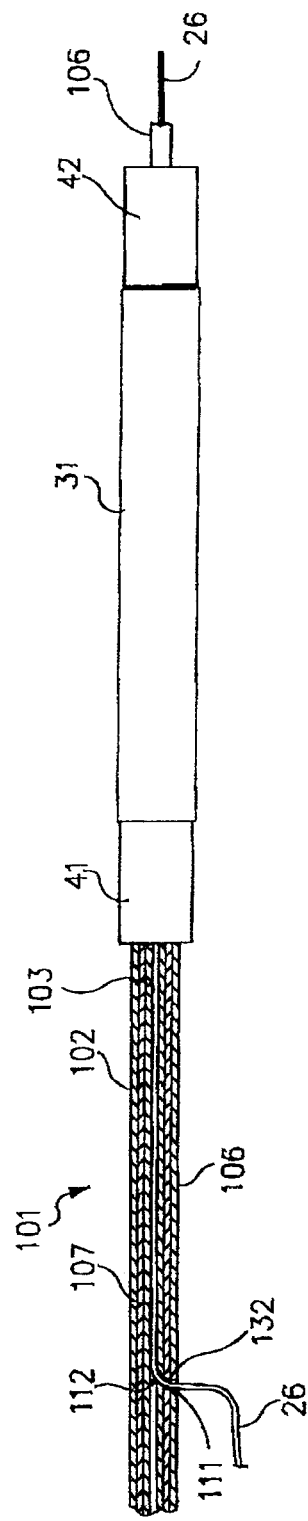
FIG. 9 is a partial side-elevational view of another embodiment of a mechanical dilatation and medicament delivery device incorporating the present invention that can be utilized in conjunction with a rapid exchange technique.
Figure 9A:
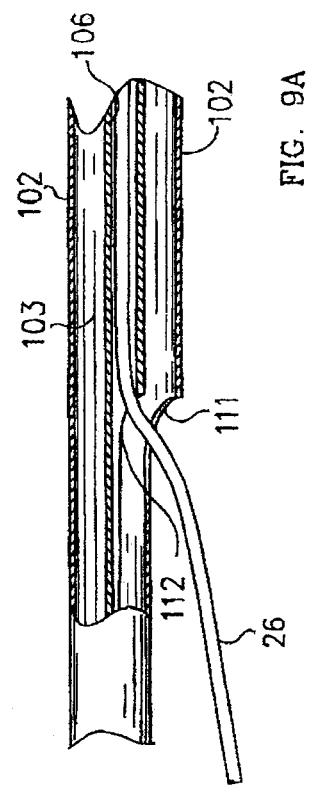
FIG. 9a is an enlarged side-elevational view of the rapid exchanged embodiment of the mechanical dilatation and medicament delivery device demonstrating the guidewire entry ports in the inner and outer elongated tubular members.

Another embodiment of a dilatation and medicament delivery device incorporating the present invention is shown in FIGS. 9 and 9a. As shown therein, the rapid exchange designed mechanical dilatation and medicament delivery device 101 is constructed in a manner similar to the mechanical dilatation and medicament delivery device 11 with the exception that it is provided with rapid exchange capabilities. This is accomplished by providing an outer flexible elongate tubular member 102 having a lumen 103 therein and an inner flexible elongate tubular member 106 having a lumen 107 which have the expansion member 31 secured thereto by the proximal and distal collars 41 and 42. The outer flexible elongate tubular member 102 is provided with a port or opening 111 into the corresponding lumen 103 and which is 13-60 centimeters from the distal extremity 32 of the expansion member 31. A corresponding port or opening 112 into corresponding lumen 107 is provided within the inner flexible elongate tubular member 106. These ports 111 and 112 are positioned so that when the expansion member 31 is in its expanded position with the distal extremities of the members 102 and 106 being in closest proximity to each other, the openings 111 and 112 are in registration with each other. In this position, the mechanical dilatation and medicament delivery device 101 can be loaded onto the guide wire 16 by advancing the most proximal extremity of guide wire 26 first into lumen 107 of the distal extremity of the inner flexible elongate member 106 and then back through port or opening 112 and port 111 which are in registration and out of the flexible elongate tubular member 102. The expansion member 31 is next contracted from its diametrically expanded condition to a contracted condition by moving the distal extremities of outer and inner flexible elongate tubular members 102 and 106 further apart by operation of screw mechanism 46. This procedure is performed while maintaining a stable position of the external position of guide wire 26 in a constant position in relation to port 111. As the distal extremity of flexible tubular member 106 is moved further from the distal extremity of flexible elongate tubular member 102, port 112 will move out of registration with port 111 while maintaining guide wire 26 within lumen 107 and advancing the distal extremity of the flexible elongate tubular member 106 along the guide wire 26. In this diametrically contracted state of the expansion member 31, the mechanical dilatation and medicament delivery device 101 may be advanced along guide wire 26 through the region of stenosis in the blood vessel and enlargement of expansion member 31 may occur using screw mechanism 46 in the manner previously described. Once dilatation and medicament delivery has been completed, expansion member 31 can be diametrically contracted and the mechanical dilatation and medicament delivery device 101 may be removed from the blood vessel and the guiding catheter by maintaining a stable position of guide wire 26 in relation to the blood vessel and retracting device 101 along guide wire 26 until the distal extremity of inner flexible member 106 exits the patient's body. The mechanical dilatation and medicament delivery device 101 may now be rapidly exchanged with another mechanical device 101 as for example, one having an expansion member 31 which can be increased to a larger diameter over a standard 175 to 185 centimeter length guide wire 26.

Figure 10:
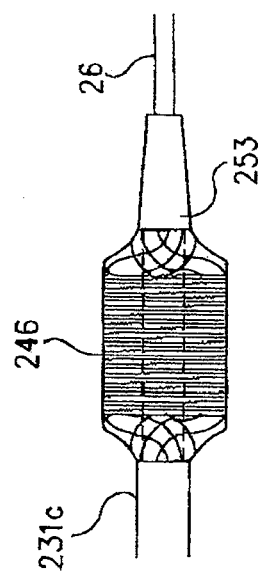
FIG. 10 is a side-elevational view of the distal extremity of the device shown in FIGS. 1-9 showing the distal extremity with the expansion member in an expanded condition.

The expansion member 31 is comprised of 16-64 individual elements formed of 0.001 to 0.005 inch diameter wire of a suitable metal such as stainless steel helically wound around a longitudinal central axis. The helices are wound in opposite directions. Stretching or elongation of the cylindrical expansion member 31 results in a reduction in diameter of the expansion member 31. Mechanical fixation of the proximal and distal extremities 22 and 23 of the expansion member 31 holds these extremities in reduced diameter configurations. The positions of the elements 21 in these extremities cannot change in relation to each other. Therefore, the crossing angles of the elements 36 remain constant. Shortening of the cylindrical expansion member 31 with the ends fixed results in the formation of a cylindrical center section of great rigidity with the elements 36 in close apposition to each other. The tapered proximal and distal extremities of the expansion member 31 causes the stresses on the individual elements 36 to be balanced. Since the proximal and distal extremities 22 and 23 are held in constant tapered positions, the interstices between the elements are maintained allowing blood to flow into and out of the cylindrical center section when the expansion member 31 is shortened as shown in FIG. 10. Shortening of the expansion member 31 results in a significant increase in the metal density per unit length in the center portion of the expansion member 31 while the metal density at the ends is relatively constant. This increase in metal density in the center section results in significant radial force generation as the elements 36 are compressed in a longitudinal direction.

As seen in FIG. 11 the flexible elongated elements 36 are designed to either passively or electrically cause the therapeutic agent or medicament 40 to dispense or migrate into the vessel wall 17. FIG. 13 demonstrates in a cross sectional view a more detailed view of one of the flexible elongate elements 36 of the expandable mesh 31 designed to either passively or electrically dispense the therapeutic agent or medicament 40 from the elongate element 36. FIG. 12 shows a cross sectional view demonstrating the dispensing of a therapeutic agent or medicament from bands 62 affixed to the inner tubular member located within the expandable mesh 31.

FIG. 14 is another cross sectional view of one of the flexible elongate elements 36 of the expandable mesh 31 demonstrating the dispensing of the therapeutic agent or medicament 40 that is incorporated within a substrate 43 over the elongate element. The substrate 43 can function to better adhere the medicament 40 to the surface of the flexible elongate element 36, time the release of the medicament into the vessel wall 17, be an agent for transferring the medicament 40 across the cell membrane boundaries either by passive or pressure mediated transfer or actively byiontophoresis or electroporation, or any combination of the services. FIG. 15 is another cross sectional view of one of the flexible elongate elements 36 of the expandable mesh 31 demonstrating the dispensing of a therapeutic agent or medicament 40 with the aid of electrical current applied to the flexible elongate elements.

FIG. 16 is a cross sectional side view of the flexible elongated elements 36 demonstrating the passive or electrically active dispensing of the therapeutic agent or medicament 40 into the vessel wall 17.

To perform as a liposome or micelle-encapsulated therapeutic agent or medicament source 40 for the present invention, the flexible elongate elements 36 themselves can be coated as described in more detail below.

A liposome or micelle-encapsulated therapeutic agent or medicament 40 can be coated on (or incorporated into a polymer or other substrate 43 and coated on the expansion mesh 31 and/or specific bands 62 mounted on the catheter located within the expansion mesh. One particular therapeutic agent or medicament 40a can be coated upon any one of the components described above, for example the expansion mesh and another therapeutic agent or medicament 40b can be coated upon another component, for example, the marker bands. Alternately, a therapeutic agent delivery lumen that has a distal port located inside the expansion member can be used to selectively release and deliver a particular therapeutic agent or medicament.

The liposome or micelle-encapsulated therapeutic agent 40 can be an anticoagulant, such as D-Phe-Pro-Arg chloromethyl ketone, an RGD peptide-containing compound, heparin, an antithrombin compound, a platelet receptor antagonist, an anti-thrombin antibody, an anti-platelet receptor antibody, aspirin, a prostaglandin inhibitor, a platelet inhibitor or a tick anti-platelet peptide.

The liposome or micelle-encapsulated therapeutic agent 40 can be a promoter of vascular cell growth, such as a growth factor stimulator, a growth factor receptor agonist, a transcriptional activator, and a translational promoter. Alternatively, the therapeutic agent 40 can be an inhibitor of vascular cell growth, such as a growth factor inhibitor, a growth factor receptor antagonist, a transcriptional repressor, a translational repressor, an antisense DNA, an antisense RNA, a replication inhibitor, an inhibitory antibody, an antibody directed against growth factors, a bifunctional molecule consisting of a growth factor and a cytotoxin, or a bifunctional molecule consisting of an antibody and a cytotoxin.

The liposome or micelle-encapsulated therapeutic agent 40 can be a cholesterol-lowering agent, a vasodilating agent, or other agents that interfere with endogenous vasoactive mechanisms. Additionally, the therapeutic agent 40 can be a smooth muscle inhibitor, such as: an agent that modulates intracellular calcium binding proteins; a receptor blocker for contractile agonists; an inhibitor of the sodium/hydrogen antiporter; a protease inhibitor; a nitrovasodilator; a phosphodiesterase inhibitor; a phenothiazine; a growth factor receptor agonist; an anti-mitotic agent; an immunosuppressive agent; or a protein kinase inhibitor.

Alternatively, the liposome or micelle-encapsulated therapeutic agent 40 may be disposed on or within a substrate or polymer 43, which can be biodegradable and adapted for slow release of the liposome or micelle-encapsulated therapeutic agent 40. A substrate or polymer 43 laden with one or more therapeutic agents 40 can be positioned on the bands, or coated on the flexible elongate elements 36.

A biodegradable substrate or polymer 43 such as polylactide, polyanhydride, polyorthoester or polyglycolide, for example can be used. In addition to synthetic polymers, natural polymers can be used, such as amino acid polymers or polysaccharides. The polymer 50 is selected depending on the therapeutic agent required, the polymer's 43 compatibility with a patient and the ultimate pharmacologic effect desired. For example, if the effect need only last a short period, a thin polymer 43 can be used with a limited amount of therapeutic agent capable of diffusing from the polymer 50 into the arterial wall or lumen of the vesicle. Alternatively, only the layer closest to the body fluid would contain the liposome or micelle-encapsulated therapeutic agent 40. Another alternative would be to use a polymer 43 which is biodegradable over a long period of time. Naturally, the opposite characteristics would be selected for a desired prolonged release.

Generally, the substrate or polymer 43 has a liposome or micelle-encapsulated therapeutic agent 40 release rate of between about 0.001 82 $\mu g/cm^2$-min and about 100 $\mu g/cm^2$-min, especially between about 0.01 $\mu g/cm^2$-min and 10 $\mu g/cm^2$-min. In addition, the substrate or polymer 43 generally has a thickness of between about 0.01 mm and 10 mm, especially between about 0.1 mm and 1.0 mm. As can be appreciated, the device 10 can be comprised of two or more different therapeutic agents 40 or two or more different polymers 43 to obtain a desired effect and release rate. In addition, the polymers 43 can have different solubilities or diffusion characteristics to accomplish non-uniform therapeutic agent 40 release.

The methodology for coating of a polymer and/or a therapeutic agent or medicament onto the bands or flexible elongate elements of the expansion member is well known to those skilled art or can be determined by reference to standard references. In addition, the characteristics of the particular substrate or polymer 43 for these purposes is well known to the skilled artisan or can be determined by reference to standard references, e.g., *Biodegradable Polymers as Therapeutic agent Delivery Systems*, R. Langer and M. Chasin, Eds., Marcel Dekker Inc., New York, N.Y., USA (1990); Engleberg and Kohn, "Physico-mechanical properties of degradable polymers used in medical applications: a comparative study," *Bionuzterials* 12:292-304 (1991); *Controlled Release Delivery Systems*, T. J. Roseman and S. D. Mansdorf, Eds., Marcel Dekker Inc., New York, N.Y., USA (1983); and "Controlled Release Technology, Pharmaceutical Applications, ACS Symposium Series, Vol. 348, P. I. Lee and W. R. Good, Eds., American Chemical Society, Washington, D.C., USA (1987).

Operation and use of the mechanical dilatation and medicament delivery device 11 may now be briefly described as follows. Let it be assumed that the patient which the medical procedure is to be performed utilizing the mechanical dilatation and medicament delivery device 11 has one or more stenoses which at least partially occlude one or more arterial vessels supplying blood to the heart and that it is desired to enlarge the flow passages through these stenoses. Typically the mechanical dilatation and medicament delivery device 11 would be supplied by the manufacturer with the cylindrical expansion member 31 in its most contracted position to provide the lowest possible configuration in terms of diameter and so that the diameter approximates the diameter of the outer flexible elongate tubular member 12 and previously coated with a therapeutic agent or medicament 40. Alternatively, the mechanical dilatation and medicament delivery device will be supplied either uncoated or coated only with the bonding polymer present on the dilatation member and without any liposome or micelle-encapsulated therapeutic agent or medicament 40 on the expansion mesh. In this example, a container having a solution of the liposome or micelle-encapsulated therapeutic agent 40 can be separately supplied whereby sometime prior to inserting the mechanical dilatation and medicament delivery device into the patient, the expansion mesh 31 is immersed or dipped into the container in order to coat the flexible elongate members 36. Appropriate time and/or temperatures will be allowed for the medicament solution to adsorb, dry and adhere to the polymer coated expansion mesh, or alternately, a charge can be applied to facilitate bonding of the medicament or therapeutic agent to the polymer coated expansion member.

Preferably, the coated expansion member 35 should have a diameter that is only slightly greater than the tubular member 12, as for example by 1.0-2.3 millimeters. The first and second collars 41 and 42 also have been sized so they only have a diameter that is slightly greater than the outer diameter of the outer flexible elongate tubular member 12. To bring the cylindrical expansion member 31 to its lowest configuration, the linear movement mechanism 46 has been adjusted so that there is a maximum spacing between the distal extremity 23 of the inner flexible elongate tubular member 21 and the distal extremity 14 of the outer flexible elongate tubular member 12. In this position of the expansion member 31, the flexible elongate elements 36 cross each other at nearly right angles so that the interstices or openings 37 therebetween are elongated with respect to the longitudinal axis.

If applicable, the present invention has the flexible elongate elements of the catheter coated with a liposome or micelle-encapsulated medicament or therapeutic agent that can be subjected to an electrical current that renders the flexible elongate members to have a charge opposite to that of the therapeutic agent or medicament. Applicable liposome or micelle-encapsulated therapeutic agents or medicaments will have inherent charge potentials that when opposite charges are applied to the expansion member, an electrical bond is established between the surface of the expansion member and the liposome or micelle-encapsulated therapeutic agent or medicament. Electrical energy or current may be applied from an electrical connector located on the proximal end of the catheter, through the leads 45 and to the coated expansion member 35. This would create a significant bonding of the liposome or micelle-encapsulated therapeutic agent or medicament 40 to the flexible elongate elements 36. The continuously charged mesh with the attached liposome or micelle-encapsulated therapeutic agent or medicament 40 could then be advanced through the patient's vasculature to the site of dilatation and therapy without significant loss of the medicament in the bloodstream.

The mechanical dilatation and medicament delivery device 11 is then inserted into a guiding catheter (not shown) typically used in such a procedure and introduced into the femoral artery and having its distal extremity in engagement with the ostium of the selected coronary artery.

Thereafter, the guide wire 26 can be inserted independently of the mechanical dilatation and medicament delivery device 11. If desired the guide wire 26 can be inserted along with the mechanical dilatation and medicament delivery device 11 with its distal extremity extending beyond the distal extremity of device 11. The guide wire 26 is then advanced in a conventional manner by the physician undertaking the procedure and is advanced into the vessel containing a stenosis. The progress of the distal extremity of the guide wire 26 is observed fluoroscopically and is advanced until its distal extremity extends distally of the stenosis. With the expansion member 31 in its diametrically contracted position and the liposome or micelle-encapsulated medicament or therpeutic agent coated thereon, the mechanical dilatation and medicament delivery device 11 is advanced over the guide wire 26. The distal extremity 23 of the second or inner flexible elongate tubular member 21 is advanced through the stenosis over the guide wire 26 until it is distal to the stenosis and so that the distal extremity 14 of the first or outer flexible elongate tubular member 12 is just proximal of the stenosis.

After the expansion member 31 is in a desired position in the stenosis, the expansion member 31 is expanded from its diametrically contracted position to an expanded position by moving the distal extremities 14 and 23 closer to each other by operation of the screw mechanism 46. This can be accomplished by holding one distal extremity stationary and moving the other distal extremity towards it or by moving both distal extremities closer to each other simultaneously. This movement of the distal extremities 14 and 23 causes collars 41 and 42 to move closer to each other and to cause the central flexible elongate elements 36 forming the double helix mesh of the intermediate portion 31a of the flexible cylindrical expansion member 31 to move relative to each other to progressively decrease the vertical crossing angle of the double helically wound flexible elongate elements 36 from approximately 140° to 170° in its extended state to 5° to 20°0 in its axially contracted state and to progressively change the interstices or openings 37 from diamond-shaped openings with long axes parallel to the central longitudinal axis of the catheter in its extended state to substantially square-shaped openings in its intermediately contracted state to elongate diamond-shaped interstices or openings with the longitudinal axes extending in directions perpendicular to the central longitudinal axis with the flexible elongate elements 36 coming into close apposition to each other while at the same time causing radial expansion of the expansion member and to progressively increase the diameter of the central flow passage 34. The enlargement of expansion member 31 in addition to being viewed fluoroscopically can also be ascertained by the indicia 68 carried by the threaded member 67.

The intermediate portion 31a of the cylindrical expansion member 31 when fully expanded is almost a solid tubular mass which has significant radial strength to fully expand a stenosis or alternatively a stent or prosthesis. In addition, because of spring-like properties of the enlarged expansion member being comprised of helically wound flexible elongate elements 36, the expansion member 31 can conform to a curve within the blood vessel while still exerting significant radial force to the stenosis or alternatively a stent or prosthesis and to make possible compression of the stenosis without tending to straighten the curve in the vessel which typically occurs with standard straight angioplasty balloon systems. Since the expansion member or alternatively a stent or prosthesis is coated with a therapeutic agent or medicament one or more therapeutic agents or medicaments can be delivered to the vessel during the time of device expansion while blood is permitted to flow unobstructed to the distal vessel (see FIGS. 11-16).

Additionally an electrical charge can be provided to the dilatation member or mesh that is opposite in charge to that used to bind the liposome or micelle-encapsulated medicament to the mesh or expansion member. This charge will then tend to drive the liposome or micelle-encapsulated medicament or therapeutic agent into the tissue through iontophoretic means. The iontophoretic process is known to facilitate or assist the transport of the liposome or micelle-encapsulated medicament or therapeutic agent across the selectively permeable membranes and enhance tissue penetration. Since the present invention involves the use of electrical energy, there are many possible waveforms contemplated for use. As depicted in FIGS. 8a-8f, square waves 61, rectangular waves 63, saw toothed waves 64, sinusoidal waves that do not reverse polarity 65, rectified sinusoidal waves, 72 and modified rectangular or other waves 73. The primary characteristic of the preferred waveforms is that they all provide a net flow of current to the coated expansion member 35. It must be appreciated by those skilled in the art, that the waveforms with frequencies and duty cycles must be capable of delivering the desired current under varying impedances encountered by the expansion member 35 and the surrounding vessel wall 17 and fluids.

After a predetermine time, the electrical current can be altered to achieve another purpose or terminated. Since blood flows continuously through the dilatation and medicament delivery device 11 during the dilatation and medicament delivery procedure, there is minimal danger of ischemia occurring. This makes it possible to maintain dilatation and medicament delivery 11 of the obstruction over extended periods of time when desired. One particularly advantage for the mechanical dilatation and medicament delivery device 11 is that it could be used with patients which have obstructions of a critical nature that cannot even tolerate relatively short periods of balloon dilatation without leading to ischemia and creating permanent damage or shock to the patient. Another advantage of the present invention is the increased contact area of the cylindrical expansion member with the vessel wall can lead to increased adsorption of the medicament or therapeutic agent by the tissues.

After dilatation and medicament delivery of the lesion has been carried out for an appropriate length of time, the expansion member 31 can be moved from its expanded position to a contracted position by, for example, operation of the screw mechanism 46 in a reverse direction to cause separation of the distal extremities 14 and 23 to thereby cause elongation of the expansion member 31 with a concurrent reduction in diameter.

After the expansion member 31 has been reduced to its contracted or minimum diameter, the mechanical dilatation and medicament delivery device 11 can be removed along with the guide wire 26 after which the guiding catheter (not shown) can be removed and the puncture site leading to the femoral artery closed in a conventional manner.

Describe below are some examples of experiments conducted using the present invention.

EXAMPLE 1

Local Delivery of 7-Amino Actinomycin D

7-Amino Actinomycin D is a fluorescent (emits at 610 nm, [red]) analog of Actinomycin D, a potent inhibitor of cellular proliferation. It is very lipophilic and poorly soluble in water. Liposome or micelles were prepared by mixing 3.0 mg of phosphatidylcholine, 3.0 mg of cholesterol and 0.3 mg of phosphatidylserine in a test tube. Chloroform (200 microliters) was added and the solution was evaporated to dryness in a test tube. 7-Amino Actinomycin D (500 mg) was dissolved in 8 mM $CaCl_2$ for a final concentration of 0.5 mg/ml. The 7-Amino Actinomycin D solution was added to the lipid mixture in small aliquots with constant stirring. The hydrogel-coated metal mesh catheter was placed in the 7-amino Actinomycin D/liposome or micelle mixture and then used for drug delivery in the following manner: The hydrogel-coated metal mesh catheter was placed in the 7-Amino Actinomycin D/liposome or micelle mixture and then removed. In some cases, the hydrogel-coated mesh portion of the catheter was covered with a retractable sheath to prevent loss of the compound during the transport of the catheter from the arterial access site to the target site. When the catheter was positioned at the target site the sheath was retracted and the mesh was expanded against the arterial wall. Iontophoersis was performed by applying an electrical current to the mesh. The circuit was completed by pacing a patch on the skin that was connected to the circuit and had an opposite charge than the mesh. In this example the iontophoresis parameters were 5 mA, and 8 V, applied for 10 minutes. The results also show 7-Amino Actinomycin D throughout the vessel wall and in the outer layer of the vessel. There is also evidence of localization of the 7-Amino Actinomycin D in the nuclei of the cells.

EXAMPLE 2

Local Delivery of Paclitaxel

Paclitaxel is one of the most potent inhibitors of cellular proliferation in clinical use and has been shown to be efficacious in a large number of cancers. Paclitaxel is very lipophilic and essentially insoluble in water. Liposome or micelles were prepared by mixing 0.72 mg phosphatidylcholine and 0.8 mg of phosphatidylserine in a test tube with 800 microliters of chloroform. The solution was evaporated to dryness. Paclitaxel labeled with a fluorescent probe (Oregon Green) was dissolved in methanol to obtain a 20 1 mg/1 ml solution. Twenty-five microliters of this solution was combined with 975 microliters of 8 mM $CaCl_2$. The paclitaxel solution was added to the dried lipid mixture in small aliquots with constant stirring. The hydrogel-coated metal mesh catheter was placed in the paclitaxel/liposome or micelle mixture and then removed. In some cases, the hydrogel-coated mesh portion of the catheter is covered with a retractable sheath to prevent loss of the compound during the transport of the catheter from the arterial access site to the target site. When the catheter was positioned at the target site the sheath was retracted and the mesh was expanded against the arterial wall. Iontophoersis was performed by applying an electrical current to the mesh. The circuit was completed by pacing a patch on the skin that was connected to the circuit and had an opposite charge than the mesh. In this example the iontophoresis parameters were 7 mA and 8

V, applied for 20 minutes. The results showed the paclitaxel throughout the vessel wall and in the outer layer of the vessel.

Although, the procedure hereinbefore described was for treatment of a single stenosis, it should be appreciated that if desired during the same time that the mechanical dilatation and medicament delivery device 11 is within the guiding catheter, other vessels of the patient having stenoses therein can be treated in a similar manner merely by retracting the distal extremity of the mechanical dilatation and medicament delivery device 11 from the stenosis being treated, placing another prosthesis over the expansion member, and then advancing it into another stenosis in another vessel in a similar manner.

The advantages of using the present invention is the ability to deliver a liposome or micelle-encapsulated therapeutic agent or medicament to a vascular segment for prolonged periods while allowing continuous perfusion of blood into the distal to the treatment area.

From the foregoing, it can be seen that there has been provided a mechanical dilatation and medicament delivery device which can be used in a similar manner to a balloon catheter in dilating a vessel segment or deploying a stent during an interventional procedure with the outstanding advantage that blood can continue to flow to the distal blood vessel during the procedure while delivery of a liposome or micelle-encapsulated medicament or therapeutic agent is also accomplished. This permits a longer vessel dilatation and medicament delivery without tissue ischemia. Furthermore, the dilatation and medicament delivery device provides either passive or active delivery of a medicament or therapeutic agent to the affected vessel walls via the coated expansion member or via a stent or prostheis coated with such an agent. Furthermore, the mechanical dilatation and medicament delivery device also provides the advantages of known expanded non-compliant diameter and therefore exact sizing.

We claim:

1. An apparatus for delivering a medicament or therapeutic agent to an obstruction within a vascular segment or a body passageway which comprises:
    a catheter having a distal end and a proximal end;
    a substantially cylindrical shaped expansion member located on the distal end of the catheter, the expansion member including first and second ends and having a plurality of flexible elongate elements, the plurality of flexible elongate elements comprising:
        a first set of elements having a first common direction of rotation crossing a second set of elements having a second common direction of rotation opposite to that of the first direction of rotation to form a double helix mesh;
    altering means engageable to said first and said second ends of said expansion member for altering a distance therebetween to move said expansion member between a first configuration wherein said expansion member has a first diameter and a second configuration wherein said expansion member has a first second diameter, said second diameter being greater than said first diameter;
    at least one electrical leads extending throughout the longitudinal length of said catheter, in electrical communication with, and engaged to said expansion member; and
    one or more micelles encapsulated with medicament or therapeutic agent coated on said expansion member.

2. An apparatus as recited in claim 1, wherein said expansion member defines a flow passageway extending between said first end and said second end of the expansion member.

3. An apparatus as recited in claim 1, wherein said expansion member is adapted to allow blood perfusion while said expansion member is either in said first diameter or in said second diameter.

4. An apparatus as recited in claim 1, wherein said electrical lead can communicate electrical energy to said expansion member to compel said medicament or therapeutic agent into target tissues by iontophoretic means.

5. An apparatus as recited in claim 1, wherein said electrical lead can communicate electrical energy to said expansion member to compel electroporation transfer of said medicament or therapeutic agent into target tissues.

6. An apparatus as recited in claim 1, wherein said electrical lead can communicate electrical energy to said expansion member to cause both iontopheric and electroporation transfer of said medicament or therapeutic agent into target tissues.

7. An apparatus as recited in claim 1, wherein said electrical lead can communicate electrical energy to said expansion member to cause said medicament or therapeutic agent to electrically bond to said expansion member.

8. An apparatus as recited in claim 1, wherein said micelle encapsulated with medicament or therapeutic agent is a compound that inhibits cellular proliferation, Paclitaxel, Rapamycin, Actinomycin D, Methotrexate, Doxorubicin, cyclophosphamide, and 5-fluorouracil, 6-mercapatopurine, 6-thioguanine, cytoxan, cytarabinoside, cis-platin, chiorambucil, busulfan, and any other drug that can inhibit cell proliferation, and combinations thereof.

9. An apparatus as recited in claim 1, further comprising a plurality of said micelles encapsulated with medicament or therapeutic agent coated on at least a portion of said expansion member.

10. An apparatus as recited in claim 1, wherein said electrical lead can communicate electrical energy to said expansion member in wave forms which may reverse polarity while providing a net flow of current in a desired direction.

11. An apparatus as recited in claim 1, wherein said electrical lead can communicate electrical energy to said expansion member in coordination with a patients electrocardiogram so that energy is only provided during certain phases of cardiac depolarization.

12. An apparatus as recited in claim 1, wherein the altering means is a linear movement mechanism including a Y-adapter.

13. An apparatus as recited in claim 12, wherein the Y-adapter includes a central arm having a lumen through which an inner flexible elongate tubular member extends.

14. An apparatus as recited in claim 1, wherein said micelle encapsulated with medicament or therapeutic agent is disposed within a polymer.

15. An apparatus as recited in claim 1, wherein said micelle encapsulated with medicament or therapeutic agent is charged.

16. An apparatus as recited in claim 1, wherein said micelle encapsulated with medicament or therapeutic agent is coated in bands on the expansion member.

17. An apparatus as recited in claim 1, wherein said micelle encapsulated with medicament or therapeutic agent is coated on radiopaque marker bands disposed on the expansion member.

18. An apparatus for delivering a medicament to an obstruction within a vascular segment or a body passageway which comprises:
- a catheter having a distal end and a proximal end;
- a substantially cylindrical shaped expansion member located on the distal end of the catheter, the expansion member including first and second ends and having a plurality of flexible elongate elements, the flexible elongate elements comprising:
  - a first set of elements having a first common direction of rotation crossing a second set of elements having a second common direction of rotation opposite to that of the first direction of rotation to form a double helix mesh;
- a movement mechanism which causes axial movement of collars towards one another, the collars engaging said first end and said second ends of said expansion member for altering a distance therebetween to move said expansion member between a first configuration wherein said expansion member is characterized by a first diameter and a second configuration wherein said expansion member is characterized by a second diameter, said second diameter being greater than said first diameter;
- at least one electrical lead extending through the longitudinal length of said catheter, in electrical communication with, and engaged to said expansion member; and
- one or more micelles encapsulated with medicament or therapeutic agent coated on at least portions of the first and second ends and middle portion of said expansion member,
- wherein said electrical lead can communicate electrical energy to said expansion member to cause both iontopheric and electroporation transfer of said medicament or therapeutic agent into target tissues.

19. An apparatus for delivering a medicament to an obstruction within a vascular segment or a body passageway which comprises:
- a catheter having a distal end and a proximal end;
- a substantially cylindrical shaped expansion member located on the distal end of the catheter, the expansion member including first and second ends and having a plurality of flexible elongate elements, the flexible elongate elements comprising:
  - a first set of elements having a first common direction of rotation crossing a second set of elements having a second common direction of rotation opposite to that of the first direction of rotation to form a double helix mesh;
- a movement mechanism which causes axial movement of collars towards one another, the collars engaging said first end and said second ends of said expansion member for altering a distance therebetween to move said expansion member between a first configuration wherein said expansion member is characterized by a first diameter and a second configuration wherein said expansion member is characterized by a second diameter, said second diameter being greater than said first diameter;
- at least one electrical lead extending through the longitudinal length of said catheter, in electrical communication with, and engaged to said expansion member; and
- one or more micelles encapsulated with medicament or therapeutic agent coated on at least portions of the first and second ends and middle portion of said expansion member,
- wherein said electrical lead is adapted to communicate electrical energy to said expansion member to cause said medicament or therapeutic agent to electrically bond to said expansion member.

* * * * *

UNITED STATES PATENT AND TRADEMARK OFFICE
CERTIFICATE OF CORRECTION

PATENT NO. : 7,292,885 B2
APPLICATION NO. : 10/135709
DATED : November 6, 2007
INVENTOR(S) : Scott et al.

It is certified that error appears in the above-identified patent and that said Letters Patent is hereby corrected as shown below:

On the Title Page Item (57)
Abstract, line 10, "configuration to" should be changed to --configuration and--;
Column 1, line 41, "that a certain" should be changed to --that certain--;
Column 1, line 49, "deliver a" should be changed to --deliver--;
Column 2, line 3, "means passive" should be changed to --means, passive--;
Column 2, line 6, "electrically" should be changed to --electricity--;
Column 2, line 15, "bonds the drug" should be changed to --bonds to the drug--;
Column 2, line 17, "have" should be changed to --having--;
Column 2, line 41, "agents delivered" should be changed to --agents being delivered--;
Column 3, line 10, "delivery" should be changed to --deliver--;
Column 4, line 6, "proloned" should be changed to --prolonged--;
Column 4, line 10, "an over-the-wire" should be changed to --over-the-wire--;
Column 4, line 33, "liposome or micelles or micelles" should be changed to --liposomes or micelles--;
Column 4, lines 33-34, "liposome or micelles and micelles" should be changed to --liposomes and micelles--;
Column 4, line 36, "liposome" should be changed to --liposomes--;
Column 4, line 40, "liposome" should be changed to --liposomes--;
Column 4, line 55, "segment, 3)" should be changed to --segment, and 3)--;
Column 5, line 48, "view of the one" should be changed to --view of one of the--;
Column 6, line 38, "have" should be changed to --having--;
Column 7, lines 6-7, "FIGS. 2a, 3a, 5a, and 6a" should be changed to --FIGS. 2, 3, 5 and 6--;
Column 7, line 22, "and have generally" should be changed to --and generally--;
Column 7, line 27, "electircal" should be changed to --electrical--;
Column 7, line 63, "from" should be changed to --form--;
Column 8, line 5, "elctrocardiogram" should be changed to --electrocardiogram--;

UNITED STATES PATENT AND TRADEMARK OFFICE
CERTIFICATE OF CORRECTION

PATENT NO. : 7,292,885 B2
APPLICATION NO. : 10/135709
DATED : November 6, 2007
INVENTOR(S) : Scott et al.

It is certified that error appears in the above-identified patent and that said Letters Patent is hereby corrected as shown below:

Column 9, line 13, "polybutylterphalate" should be changed to --polybutylterephthalate--;
Column 9, line 14, "invention an" should be changed to --invention, an--;
Column 13, lines 13-14, "byiontophoresis" should be changed to --by iontophoresis--;
Column 14, line 45, "skilled art" should be changed to --skilled in the art--;
Column 16, "20°0" should be changed to --20 °--;
Column 17, line 66, "Describe" should be changed to --Described--;
Column 18, line 29, "pacing" should be changed to --placing--; and
Column 19, line 33, "prostheis" should be changed to --prosthesis--.

Signed and Sealed this

Third Day of March, 2009

JOHN DOLL
*Acting Director of the United States Patent and Trademark Office*